United States Patent
Klün et al.

(10) Patent No.: US 6,469,521 B1
(45) Date of Patent: Oct. 22, 2002

(54) METHOD FOR MEASURING THE STATE OF OILS OR FATS

(75) Inventors: Wolfgang Klün, Ingolstadt; Willem Geul, Borne, both of (DE)

(73) Assignee: Ebro Electronic GmbH & Co. KG, Ingolstadt (DE)

( * ) Notice: Subject to any disclaimer, the term of this patent is extended or adjusted under 35 U.S.C. 154(b) by 0 days.

(21) Appl. No.: 09/556,164

(22) Filed: Apr. 21, 2000

(30) Foreign Application Priority Data

Apr. 22, 1999 (DE) .......................... 199 18 213

(51) Int. Cl.[7] .......................... G01R 27/26; G01R 27/08
(52) U.S. Cl. .......................... 324/658; 324/698
(58) Field of Search .......................... 324/658, 663, 324/668, 669, 670, 686, 690, 698, 674, 675

(56) References Cited

U.S. PATENT DOCUMENTS 3,739,265 A    6/1973  Skildum
5,592,098 A  * 1/1997  Suzuki et al. ............... 324/675
5,824,889 A   10/1998  Park et al.

* cited by examiner

Primary Examiner—N. Le
Assistant Examiner—James Kerveros
(74) Attorney, Agent, or Firm—Jenkens & Gilchrist, P.C.

(57) ABSTRACT

A measuring device (1) is suggested for determining the quality of oils or fats, in particular for being used in conjunction with the preparation of foods, which device has a simple construction and is easy to handle. It comprises a measuring head (12) on which a sensor (5) is attached which measures the electric constant of the oil. The measured value is further processed in electronics of the device and a statement about the state of the quality of the oil is made. The measuring head (12) is attached via an attachment (11) to a housing (10) containing the measuring electronics, the energy supply and a display (2) for the determined state of the oil or fat.

20 Claims, 4 Drawing Sheets

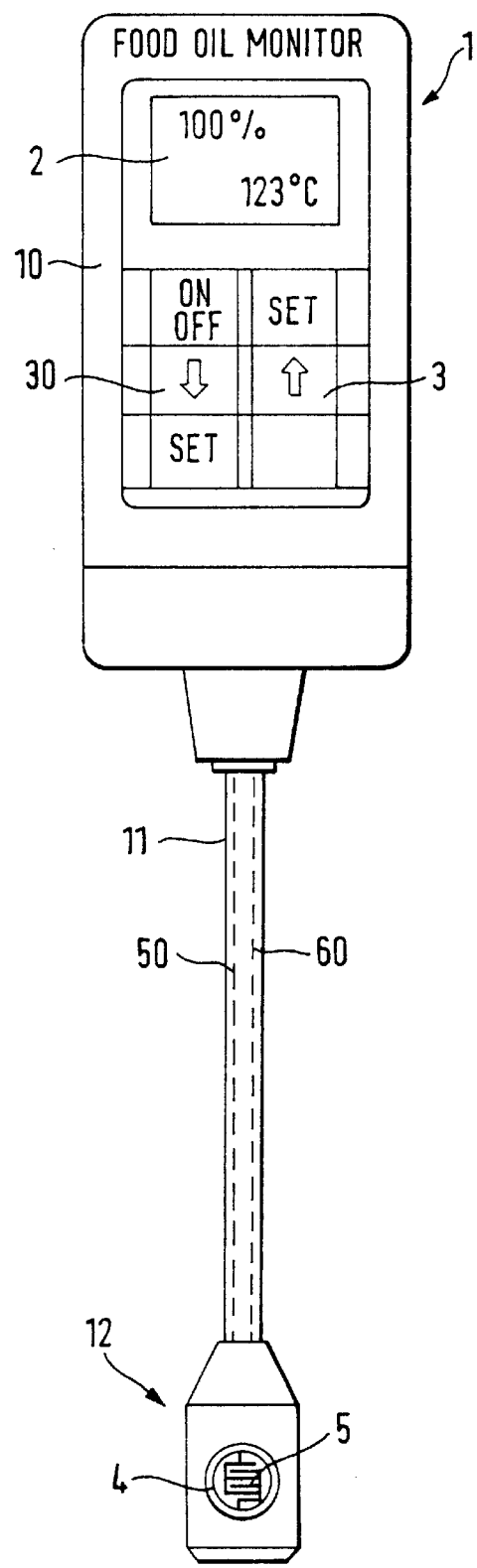
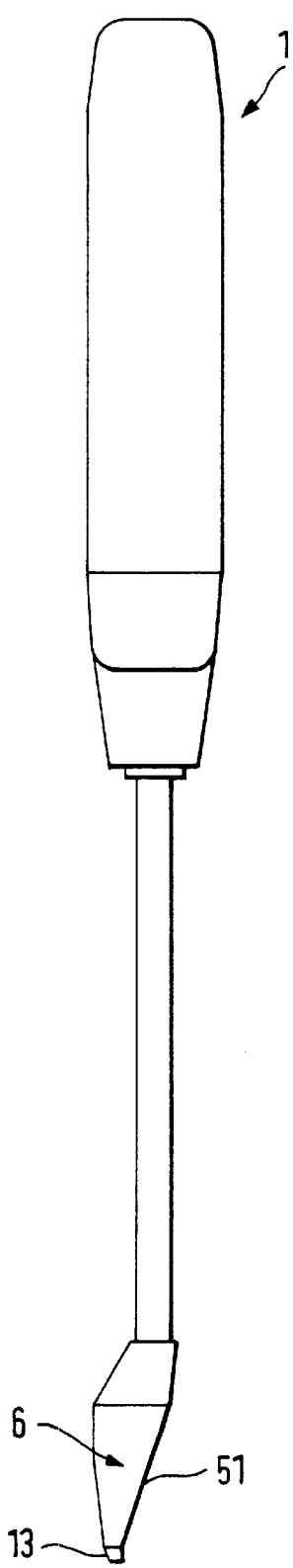

METHOD FOR MEASURING THE STATE OF OILS OR FATS

The present invention is relative to a device for measuring the state of oils or fats in accordance with the generic part of claim 1 as well as to a method for measuring the state of a measured material and to a device for carrying out the method.

Oils and fats are very important for human consumption and in particular for the preparation of foods. Thus, many foods, e.g., potatoes or foods which have already been breaded are cooked in hot oils or fats by placing them into these hot fats, which makes them accessible for human consumption. (The term "fats" is intended to denote in particular a solid form of oils in this connection.) In order to cook foods the oils and fats are used in a temperature range of approximately 90° Celsius to 180° Celsius and more. These hot temperatures result in particular in a breakdown or change of the fat which increases more and more during the use of the oil.

This change is a degradation and takes place essentially by means of the oxidation of the oil or fat. Many chemical products are produced thereby such as, e.g., free fatty acids or polymers which not only negatively affect the taste of the prepared dishes but in particular contain substances with which can make one sick and make it necessary to replace such oils, that is, in particular frying fats, on a regular and timely basis. This replacement basically takes place according to criteria which have no direct connection with the chemical change, in particular with the harmful chemical change of the fat. The replacement takes place, e.g., after the passage of a certain time or after other irrelevant criteria. Thus, it occurs in practice that the fats are replaced too early or too late. The first instance produces unnecessary expense whereas a replacement that is too late entails the dangers cited above.

U.S. Pat. No. 3,739,265 teaches a test instrument which checks fat with a sensor to see whether it can still be used. Provision is made thereby to check the oil for its electric properties, in particular its dielectric properties. The test device comprises to this end a key-shaped carrier with a sensor arranged on its bottom which sensor is designed as a capacity sensor. To this end a certain amount of oil is placed on the sensor and the capacity measured with this system is processed in an electric circuit which yields a value- which makes a statement about the degree of degradation of the fat. In addition, a comparison is carried out between the fat or oil to be tested and a standard liquid which must also be measured in a measuring process. The change in the capacity of the sensor is a measure for the degree of degradation of the oil.

U.S. Pat. No. 5,824,889 teaches an oil sensor operating on a capacitive basis for measuring the degradation and contamination of oil. This sensor is used for checking the oil of internal combustion engines. The electric properties of the motor oil form a reference point for the degradation of the oil and for its still sufficient quality. The dielectric constant of a certain oil brand changes thereby within quite specific limits which were determined by tests and therefore yields a measurement for the degradation of the oil.

In addition, motor oil can also be degraded in its quality by other factors, e.g., by the presence of contaminants, e.g., by cooling liquids or gasoline. This can also be a measure of how far the wear on the engine has progressed and of what type it is. Since, e.g., cooling liquid has a significantly higher dielectric constant a significantly higher change of the dielectric constant can be an indication of engine wear.

The sensor described in the U.S. patent for measuring the properties of the oil of internal combustion engines comprises a sensor surface mounted in the oil, e.g., in the oil pan of a motor vehicle. Only a narrow slot is provided on the sensor which permits the passage of oil to the sensor.

The disadvantage of the first-named device is that in order to measure the oil the oil must be filled into a receiving device of an oil sensor. To this end the oil must be removed, e.g., from a deep fat flyer and introduced into the measuring receptacle of the sensor. After its electrical properties have been measured the oil is removed again and the measurement carried out with a reference oil for comparison with the first measurement. Since the oil is present thereby in a very small amount it cools off very rapidly which creates the danger in the case of fats that they become hard, which falsifies the measurement or makes it impossible.

In addition, the manipulation is problematic and the oil used for the measurement must subsequently be removed so that on the whole the process is time-consuming and unpleasant. This device is not suitable for use in practice, that is, without great expense. The device is not suitable for being used directly in the kitchen for directly checking the fat used without preparatory work.

The sensor of U.S. Pat. No. 5,824,889 is not only very bulky on account of its intended uses and not suitable for being used at various locations but it also has the disadvantage that the sensor surface has a covering which makes it difficult for the oil to reach the sensor when the sensor is used at other opportunities. In addition, it would be practically impossible to clean the sensor since this would be too expensive. In particular, this eliminates its being used in conjunction with food fats.

The present invention has the problem of suggesting a measuring device and a method of its operation which device avoids the disadvantages of the state of the art and is suitable by virtue of its easy handling and a suitable measuring method not only for being used under laboratory conditions but can be used in a very variable manner on account of its ability to be handled and operated very simply. In particular, the use of the device in accordance with the invention in the area of measurements, e.g., of frying oils or frying fats should be created without these oils or fats having to be first removed from the pan for measuring.

In addition, the invention should create a device which can be used in a flexible manner which can also be used for determining the quality of other oils, e.g., motor oil. Another target of the invention is to create a measuring device with an oil sensor which can be used in a mobile fashion, that is, without the sensor having to be permanently installed for measuring or having to be integrated in the oil container. In addition, a method should be created which yields precise results.

The design of the measuring device in accordance with the invention brings it about that a device is created which is easy to handle, manipulate and can be reliably operated even when dealing with hot liquids. In addition, it has the advantage that it supplies reliable measured results independently of the temperature of the matter to be measured and without preparatory measures being required in order to be able to use the device. The fact that the attachment is designed as a rod-shaped or tubular element brings it about in an advantageous manner that the measuring head and the housing are rigidly connected to one another so that only one hand is required for operating the measuring device. The handling of flexible cables is eliminated. A reliable handling of the measuring device is assured. In addition, the attachment makes it possible for the operator of the measuring device to be assured in an advantageous manner of a safe interval between the matter to be measured and his hand, which guides the measuring device on the housing. The connection between the measuring head and the evaluation electronics takes place in an advantageous manner via the interior of the attachment.

The designing of the measuring device with a compensator brings it about in an advantageous manner that changes of the sensor itself caused by a change in temperature are compensated. This makes it possible to use the measuring device at different temperatures in a simple and economical manner without expensive methods requiring an adjustment of the device to different temperatures being necessary.

In a particularly advantageous manner the compensator has the same design as the sensor itself This makes it especially simple and reliable to integrate the compensator into the evaluation electronics as regards the circuitry without further additional measures being necessary. In an especially advantageous manner the compensator is designed just as the sensor is. This assures a reliable statement about the state of the oil or fat. The sensor advantageously comprises two electrodes to this end of which at least one consists of a thin metal wire. The term "wire" in this context also denotes a printed circuit. To this end, e.g., gold is applied in the form of a circuit and subsequently fixed on the carrier plate. This can take place, e.g., by burning it in. This makes it possible in an advantageous manner to produce the sensor in a precisely reproducible manner and also to simply and reliably arrange it on a carrier.

A gold wire proved to be especially advantageous. In a quite particularly advantageous manner the carrier plate consists of a ceramic material since this material is chemically neutral and has good properties as regards thermal expansion. In addition, it has the particular advantage when the measuring device is to be used with foods such as, e.g., frying fats that ceramic material, in particular, is food-proof, that is, can be safely used with foods. It is particularly advantageous to use a material for the measuring device which is heat-resistant up to above 200° Celsius, especially up to above 230°. This assures that the measuring device can be reliably used without being destroyed by the temperature of the material to be measured.

The measuring head advantageously comprises a cover for the sensor so that the latter cannot be destroyed by mechanical contacts. This cover is advantageously designed in such a manner that it is constructed as an edge of the attachment. This is achieved in an especially advantageous and simple manner in that the attachment is cylindrically designed and terminates with an oblique surface. This protects the sensor from contacts and at the same time makes it readily assessable in particular for cleaning measures.

In a particularly advantageous further development of the invention a display is associated with the output unit of the measuring device via which display one can optically recognize in a simple manner which parameters are set on the measuring device and what the result of measuring is. This result is displayed in an especially advantageous manner as a numeric value or graphically, e.g., as a bar graph in which case the output unit is designed in such a manner that it can be adjusted to selectively show the result of measuring.

The measuring device is advantageously designed with an evaluation electronics associated with storage means for storing, e.g., configuration data, calibration data of the measuring device or correction data. As a result thereof the measuring device can operate in a particularly exact and advantageous manner especially, e.g., by means of specific data regarding certain oils. Data from test series is integrated into the storage means thereby so that specific deviations and changes in the dielectric constants of various commercial fats and oils can be taken into account in order that the measuring device can operate in an especially precise manner.

In a particularly advantageous embodiment of the invention the evaluation and control electronics comprises a microcontroller which assures that the measuring device can operate reliably, simply, rapidly and flexibly. In particular, correction data can be managed simply and quite precisely with the aid of a microcontroller. To this end the measuring device also comprises in an especially advantageous manner an input unit for entering data and an output unit for outputting the result of measuring so that additional information can be entered into the measuring device by the operating person and that this can also be controlled, e.g., via the output unit, which creates a device which can be set and adjusted for different areas of use in a flexible manner.

For storing data the measuring device advantageously comprises an EEPROM, which makes possible a rapid and extensive storage of data. In an especially advantageous further development of the invention the measuring head additionally comprises a temperature sensor so that the device can also be used at the same time in an advantageous manner for measuring the temperature of the material to be measured. The temperature sensor and/or the measured temperature can also be advantageously used to set up correction values, if this is necessary, which can then make the result of measuring even more precise.

The design in accordance with the invention of the method for measuring the state of the material to be measured brings it about that a compensation of temperature-related changes of the measured value of the sensor can be compensated simply and reliably. As a result of the fact that the compensation takes place electronically directly in the measuring bridge expensive additional measures are not necessary. As a result thereof, the electronics is so simply designed that it corrects itself. Expensive control and regulating measures within an evaluation electronics are eliminated. As a result of the fact that the compensation unit is also advantageously designed as a capacitor the compensation is achieved in a reliable manner. In an advantageous further development of the method the compensation unit is exposed at the same time to the same temperature as the sensor itself during the measurement. This is achieved in particular in an advantageous manner in that the compensation unit is arranged on the same carrier as the sensor itself, which reliably assures that the compensator is exposed to the same temperature.

A compensation is achieved in an especially advantageous manner if the compensation unit is designed equally to the sensor. This excludes, e.g., differences in manufacture and different reactions of an electronic component due to a different spatial design. This renders the method especially simple and reliable and a device can be manufactured in an especially simple manner.

A microcontroller is used with particular advantage for controlling the measuring bridge and for detecting the values of the measuring bridge. This makes possible a fine control of the measuring bridge and detection of the results of measuring.

The device in accordance with the invention for carrying out the method assures that the method can be reliably carried out. The device is designed in an especially advantageous manner if the compensator is arranged on a carrier which, e.g., makes contact with the material to be measured in such a manner that the temperature of the material to be measured is also reliably transferred to the compensator. The device is designed in an especially simple and advantageous manner in that a carrier is used which carries the sensor on the one side and the compensator on the back side. As a result thereof both exactly determine the temperature of the material to be measured via the carrier. This makes a very precise measurement possible.

As a result of the equal construction of the capacitor and the compensator the method is reliably carried out by the device and no further measures and devices are required for achieving a compensation. The device is provided in an especially advantageous manner with a microcontroller which controls the measuring bridge in a simple, reliable and versatile manner. This microcontroller already contains analog and digital converters in an advantageous manner so that no additional components are required. The microcontroller contains direct connections which are capable of converting the analog measured value supplied by the measuring bridge directly into a digital value which can also be further processed by the microcontroller. Inversely, it is just as advantageous if the microcontroller also comprises connections at the same time which supply the control signals of the microcontroller in analog form already for controlling the measuring bridge so that they can be furnished to the measuring bridge.

In an especially advantageous further development of the invention the device in the measuring head additionally comprises a temperature sensor which creates additional information as well together with the output unit for the operating person. It is moreover possible that the temperature values of the temperature sensor from the microcontroller are used for purposes of control and compensation.

The invention is explained in the following with reference made to the drawings.

FIG. 1a shows a measuring device in accordance with the invention.

FIG. 1b shows a lateral view of FIG. 1a.

Figure 2:
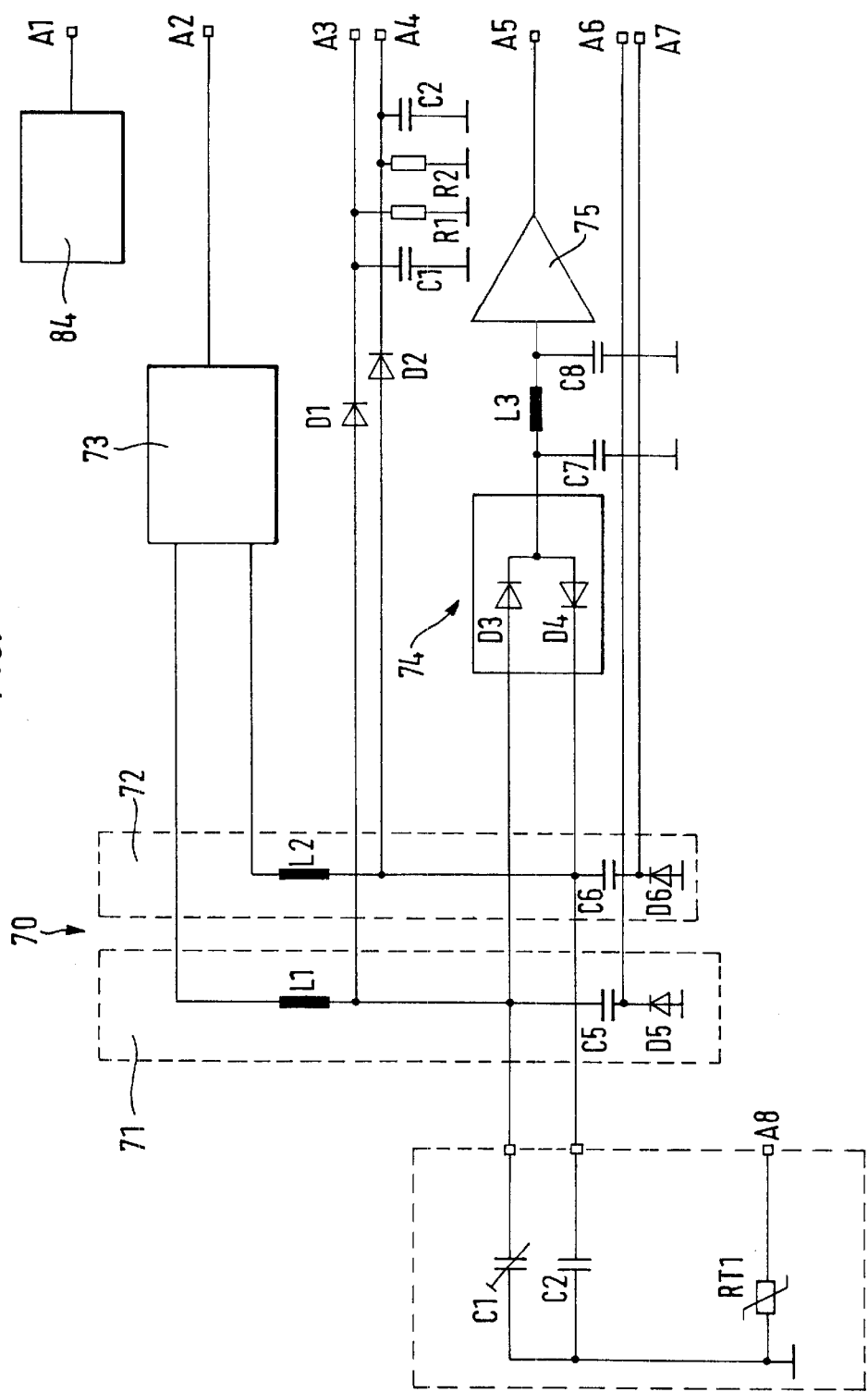
FIG. 2 shows measuring electronics 7 for the measuring device of FIG. 1.

FIGS. 1a and 1b show measuring device 1 designed in accordance with the invention for measuring the state of a material to be measured, especially for measuring oils and fats. The measuring device consists of housing 10, attachment 11 and measuring head 12. Housing 10 contains display 2, visible from the outside, for displaying the measured value. Display 2 is designed in the form of an LCD display and can be switched, depending on the operation of measuring device 1, between different representations, e.g., graphic representation or representation by means of numerical values. The switching to different types of display takes place via input unit 3 designed in the form of keypad 30. The other parts of the housing simultaneously form a grip for an operating person to grasp measuring device 1.

Housing 10 is followed by attachment 11 forming a connection between measuring head 12 and housing 10. Attachment 11 consists of a thin-walled tube of noble steel, e.g., V4A. Attachment 11 has the task of creating a separation between measuring head 12 and housing 10 with the control electronics contained in it. Attachment 11 makes it possible to design measuring device 1 as a compact unit in which measuring head 12 and the display device with evaluation electronics are separated spatially from each other but can both be operated with one hand.

The sensors customary in the state of the art, which are connected by a cable to their measuring electronics, are significantly more difficult to manage in comparison to measuring device 1. At the same time attachment 11 has the function of holding measuring head 12 on measuring device 1 in such a manner that when measuring device 1 is used there is such interval between measuring head 12 and housing 10 that the evaluation electronics in housing 10 is sufficiently far removed from the temperature of the material to be measured as well as the hand of the operating person guiding measuring device 1 via housing 10 during the measurement. As a result of the property of noble steel of being a poor heat conductor it is achieved in measuring device 1 in conjunction with the length of attachment 11 that even if measuring head 12 remains for a rather long time in hot oil housing 10 is not affected by the temperature. Electric leads run inside attachment 11 which connect measuring head 12 to the electronics inside housing 10.

Measuring head 12 consists essentially of a ceramic plate set in the open end of attachment 11. Ceramic plate 4 seals off the lower end of attachment 11 since the ceramic plate is set into the noble steel tube of attachment 11 in a completely sealing manner. The ceramic plate has an oval shape since tubular attachment 11 was cut with a cut which does not run vertically to the axis of attachment 11. The cut and thus also ceramic plate 4 run at an angle of approximately 45° to the longitudinal axis of attachment 11.

Sensor 5 is positioned on ceramic plate 4. Sensor 5 is designed as a capacitive sensor comprising two essentially identical electrodes consisting of a fine gold wire placed in loops. Sensor 5 is placed on side 51 of ceramic plate 4 facing the material to be measured. It consists of gold threads applied to the surface with a thermal process. A second capacitor with the same design as sensor 5 and consisting of the same material is applied in the same manner to the other side of ceramic plate 4 and is therefore not visible in FIGS. 1a and 1b. This capacitor applied to the back side of ceramic plate 4 functions as compensator 6. Sensor 5 and compensator 6 are connected via associated electrical leads 50 and 60 to the electronic circuit of measuring device 1. Compensator 6 does not make contact with the material to be measured.

The method of operation of measuring device 1 is as follows: The device is first turned on with keypad 30 of input unit 3 by the operating person. After having been turned on, a null balance of the sensor against air takes place at first, that is, the sensor has not yet been inserted into the material to be measured. After release by the control unit, which is indicated in display 2, the actual measuring process can begin. At first the type of the oil to be measured is entered via input unit 3 and then the measuring head is inserted into the liquid to be measured, that is, e.g., the hot oil. After approximately 10 seconds the measured value stabilizes in the circuit and is taken over by the device, that is, by a microcontroller located in measuring device 1 and the measured result displayed in the display, wherewith the measuring is concluded. During the measuring measuring device 1 is held by the operating person on housing 10.

Sensor 5 comes into direct contact with the hot fat during the measuring and as a result thereof measures the dielectric constant of the liquid fat or oil. An especially simple device which is ready to be used at all times assures this especially favorable advantage of the measuring device of the invention. It is not necessary to wait until the material to be measured has cooled off. This makes it able to be used also for fats with only become liquid at rather high temperatures. The measuring device can be used even during the ongoing operation of a frying. In order that sensor 5 is protected from damage the measuring head comprises cover 13 for sensor 5. In the present embodiment cover 13 is designed in such a manner that tubular attachment 11 is shaped obliquely to the axis of attachment 11 on its tip carrying measuring head 12.

This design makes a surface available for sensor 5 on ceramic plate 4 which surface practically does not come into contact with a wall of a container since cover 13 first makes contact either with a container wall or the container bottom so that sensor 5 therefore can not make contact. At the same time this shape of cover 13 offers an excellent possibility of nevertheless making sensor readily accessible, e.g., for cleaning ceramic plate 4 by the operator of measuring device 1.

Sensor 5 in the form of gold electrodes permanently applied onto ceramic plate 4 is not sensitive to cleaning measures. Thus, contacts with sensor 5 are generally not damaging as such so that cover 13 is completely sufficient for protecting sensor 5 when it is designed as a tip as in the present example. However, if a more sensitive sensor is used increased requirements are placed on cover 13 so that then, e.g., ribs or other measures are to be found on ceramic plate 4 in order to assure a sufficient protection for sensor 5.

As a result of the present design of sensor 5 and cover 13 measuring device 1 is therefore insensitive and well suited for being used in practice. Measuring device 1 can therefore be placed into a container practically like a cooking spoon in which container measuring device 1 stands upright with its tip, that is, cover 13 on the bottom of the container. Attachment 11 consisting, as already described above, of a tube of noble steel also contributes to the insensitivity and the suitability in practice of measuring device 1. To this end and for screening against the heat of the material to be measured attachment 11 advantageously has a length between 15 cm and 40 cm, preferably between 25 cm and 35 cm. Tubular attachment 11 advantageously has a diameter between 10 mm and 20 mm. Wires 50, 60 extend through the hollow interior of tubular attachment 11 to couple the sensor 5 with the measuring electronics 7. the heat of the material to be measured attachment 11 advantageously has a length between 15 cm and 40 cm, preferably between 25 cm and 35 cm. Tubular attachment 11 advantageously has a diameter between 10 mm and 20 mm.

FIG. 2 shows the essential elements of measuring electronics 7 with the aid of which the dielectric constant of the oil or fat to be measured is determined. Measuring electronics 7 consists of oil resonance circuit 71 with associated sensor C1 designed as a capacitor. This oil resonance circuit forms a part of measuring bridge 70 of measuring electronics 7. The second part of measuring bridge 70 is formed by compensation resonance circuit 72. The oil resonance circuit is formed by capacitor C1 (sensor C1) in contact with the oil and in addition by capacitor C5, capacitance diode D5 and inductive resistor L1.

The compensation resonance circuit consists of capacitor C2 (compensator C2), capacitor C6, capacitance diode D6 and inductive resistor L2. Both resonance circuits 71, 72 are fed from a microcontroller (see FIG. 3) with a high frequency of approximately 1 MHz to 100 kHz. However, it also turns out that a frequency in the range of approximately 50 kHz can also be used with particular advantage. The high-frequency alternating voltage is fed into measuring bridge 70 from programmable oscillator 73. In order to be able to control the resonance characteristic of both bridge branches 71, 72 an adjustable direct voltage is put on capacitance diodes D5, D6 for both circuits. As a result the latter change their capacity and therewith the resonance frequency of the associated bridge branch.

In order to be able to control the effect of the direct voltage an amplitude rectifier is contained in the circuit for both resonance circuits 71, 72. The amplitude rectifier for oil resonance circuit 71 consists of diode D1, capacitor C1 and resistor R1. For compensation resonance circuit 72 the amplitude rectifier consists of diode D2, capacitor C2 and resistor R2. The resonance characteristic of the bridge branches is controlled by the microcontroller, which engages capacitance diodes D5, D6 via connections A6, A7 with a direct voltage. The microcontroller detects the resonance characteristic of measuring bridge 70 via connections A3, A4. Oscillator 73 is controlled via connection A2.

Diodes D3, D4 form together with capacitors C7, C8 and inductive resistor L3 phase discriminator 74 which makes available the actual signal for the desired measured value on connection A5 via amplifier 75 following the phase discriminator. It is particularly advantageous if the capacitance difference of approximately $10^{-15}$ F measured by the capacitor (C1) between the unused oil and the used oil or fat yields a voltage difference of 100 mV. In order to achieve this it is advantageous to use a sensor (C1) with a sensor capacity between approximately 0.1 pF and 50 pF, preferably between 1 pF and 5 pF.

Measuring head 12 contains oil temperature sensor RT1 which is electrically supplied via measuring electronics 7. In addition, it (RT1) does not engage into the circuit of measuring bridge 70. The oil temperature is tapped off via connection A8 from the microcontroller (see FIG. 3) via a sensor interface. The current is supplied via connection A1. Alternatively, the resonance circuits and the capacitance diodes can already be contained in an integrated component.

Figure 3:
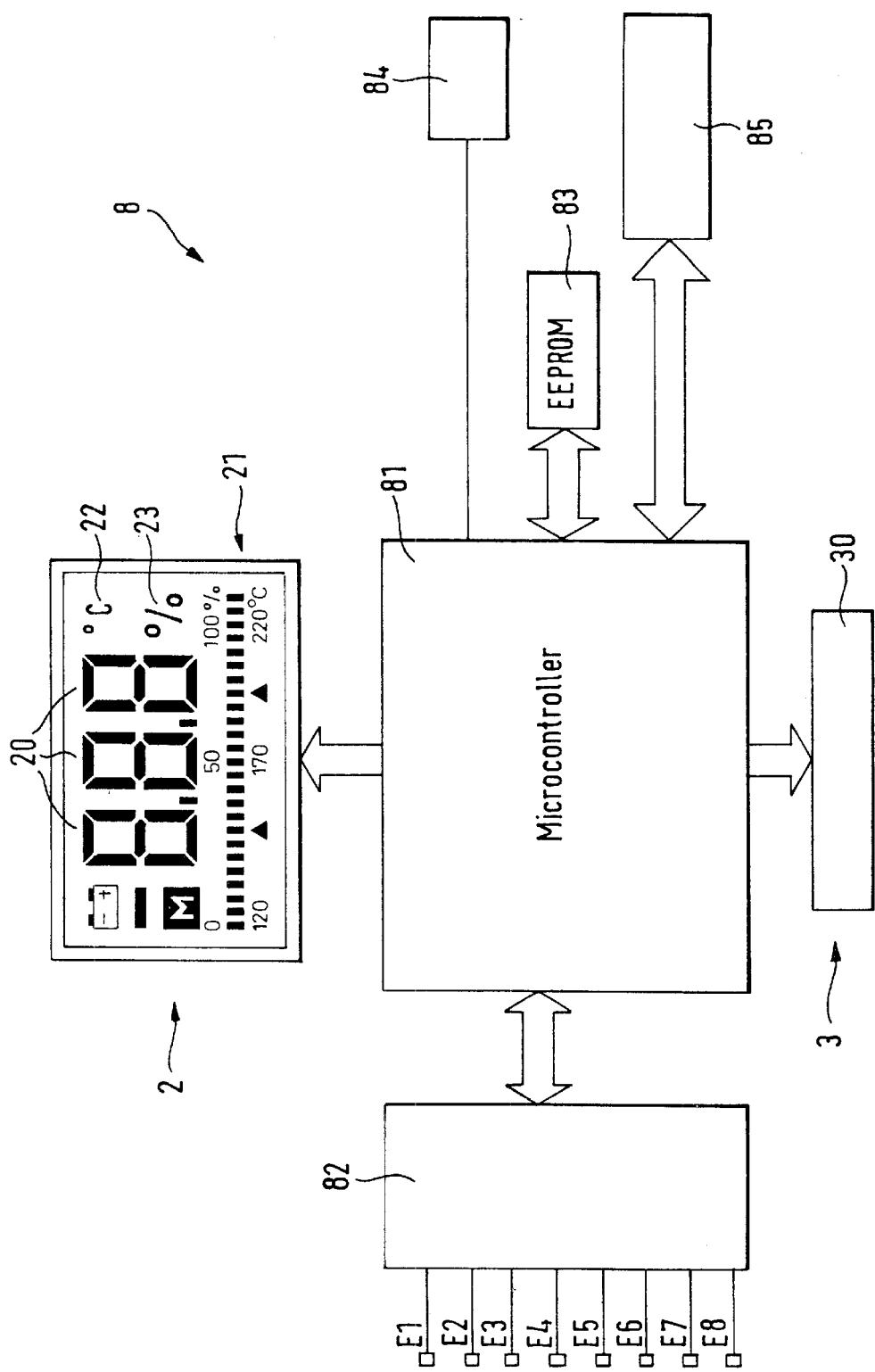
FIG. 3 shows the evaluation and control electronics for the measuring device of FIG. 1.

FIG. 3 shows a schematic view of the evaluation and control electronics 8 of the device for carrying out the measuring of the state of a material to be measured, which device is inserted in particular into a measuring device such as the one described, e.g., in FIG. 1. Evaluation and control electronics 8 basically consists of microcontroller 81. Microcontroller 81 communicates via sensor interface 82 with the measuring electronics (see FIG. 2).

Connections A1 to A8 comprise corresponding inputs E1 to E8 at sensor interface 82 of microcontroller 81. Microcontroller 81 communicates with the outside world via a keyboard, especially keypad 30, so that certain values for controlling measuring device 1 (see FIG. 1) can be entered.

EEPROM 83 is associated with microcontroller 81 for storing data, e.g. measured values or control data for correcting the measured result or correcting other control data. Moreover, microcontroller 81 comprises a connection for a current supply which is designed in particular as battery 84. The exemplary embodiment of measuring device 1 of FIG. 1 comprises, in addition, a connection at a test and programming interface to which, e.g., a PC can be connected. Test and programming interface 85 is connected for its part to microcontroller 81.

Display 2 controlled by microcontroller 81 is a very essential element of evaluation and control electronics 8. Measured results and other data from microcontroller are displayed via display 2, designed as an LCD display (see FIG. 1) to the person operating the measuring device. The LCD display of display 2 is advantageously designed to be easily readable and to make a clear statement in that it comprises numeric display 20 and an area which makes possible a display as bar graph 21. The temperature of oil temperature sensor RT1 (see FIG. 2) can be numerically displayed in a selective manner via the numeric display (see the description for FIG. 1) as well as the state of the measured material, that is, a percentage indication of to what percent the measured material is still suitable for being further used. Thus, e.g., a new oil is characterized with the value 100 representing the statement 100%.

Moreover, the information about the temperature of the oil and the state of the oil can also be shown by the range indicated by bar graph 21. Bar graph 21 consists of individual successively arrange rectangles which are all shown in black in the test image of display 2 shown in FIG. 3 and thus represent a value of 100% for the state of the oil and a temperature of approximately 240° Celsius of the oil.

If the oil has been further worn out or the temperature of the oil is lower the dark rectangles become lighter from right to left and as a result disappear. If only one-half of the rectangles are still dark from left to right they represent a value of 50% for the oil, that is, only 50% of its maximum value is still in good condition. At the same time the bar graph can display the temperature of 170° Celsius therewith. Whether a percentage value or a ° C. value is displayed by display 2 is a function of whether the ° C. sign 22 or the % sign 23 is dark.

At the same time the display also shows the state of the current supply of the measuring device. This form of the display, as the display of display 2 shows, is especially easy to read and is suitable for the mental pictures of the operator. The switching between a % display or a ° C. display or a display using bar graph 21 is selected by the operator via keypad 30.

Figure 4:
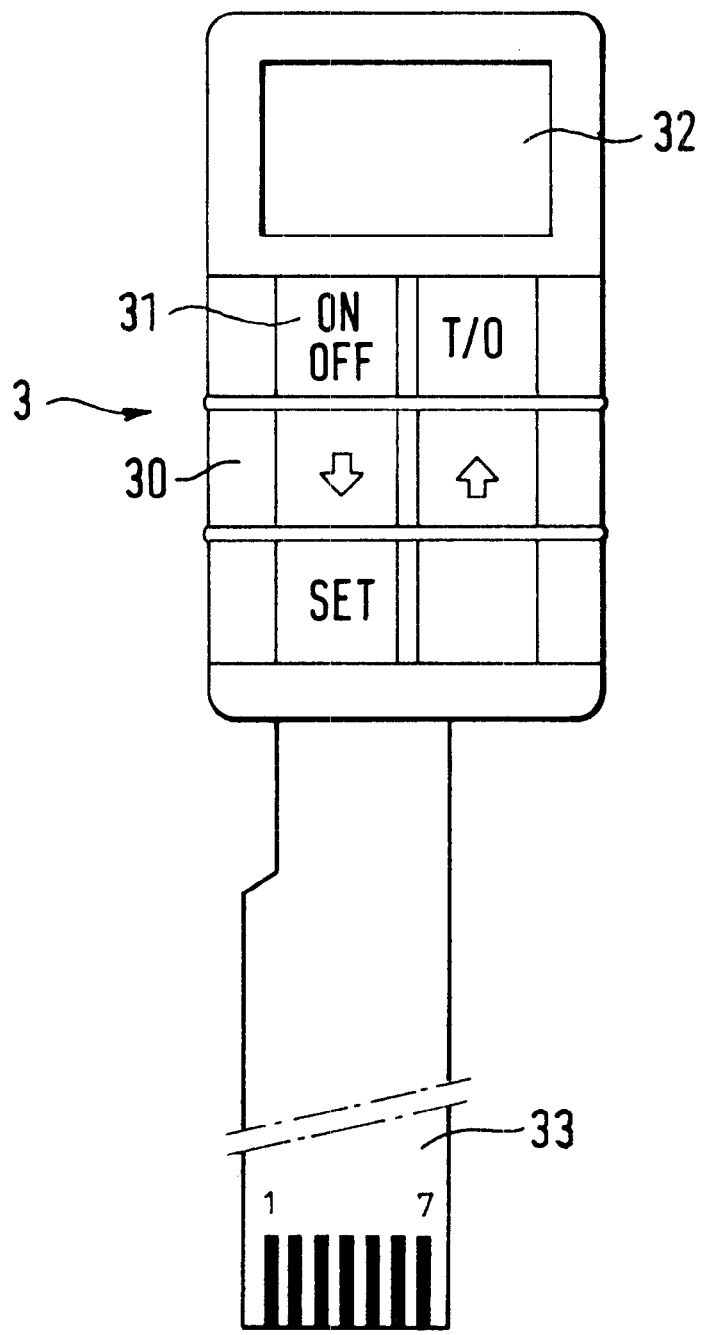
FIG. 4 shows the input unit of the device according to FIG. 1.

FIG. 4 shows inputs unit 3, designed in the form of keypad 30. It comprises recess 32 above individual keys 31 in order not to cover over display 2 (see FIG. 1). Keypad 30 comprises an on/off switch, a selector switch (T/O) and a switch for setting different input or output modes (Set). In addition, it also comprises two input keys (+and –) with which the individual modes can be browsed through and selected in the selection menu made available via the microcontroller. Keypad 30 is connected via connection 32 to microcontroller 81 (see FIG. 3).

The advantages of the invention shown in detail in the various figures and in the description of the devices and methods can be realized individually in a measuring device or, in an advantageous manner, all can be combined in one measuring device, to the extent this is practically possible. This is up to the free judgment of an expert in the art and is a function of the particular requirements on a measuring device. Thus, for example, it can be advantageous to design a measuring device in such a manner that it only has one set of configuration data in the evaluation and control electronics which permits precise statements for only one type of oil. This makes it possible to supply the device, e.g., together with one type of oil or fat to the final user so that this user can check the type of fat or oil used by him for its useful properties without adjustment measures.

In addition, it is also possible, if it should be necessary, to use the measured data of the oil temperature sensor RT1 in the microcontroller for making available configuration data for determining measured values if this should be required for an exact assignment to the temperature of the measured material.

What is claimed is:

1. A measuring device for measuring the state of a material consisting of oils or fats, especially for oils or fats for processing foods, said measuring device comprising:
a measuring head for measuring an electric quality of the material to be measured with a housing;
evaluation electronics in said housing, and an attachment extending from said housing for mounting said measuring head;
wherein the measuring head is mounted on said attachment so that a spatial separation of the measuring head and the evaluation electronics is produced, and so that the influences due to the measurement, such as temperature influences on the measuring head do not affect the measuring electronics located in the housing.

2. The measuring device of claim 1 wherein the attachment is a tubular element connected on its one end to the housing, the measuring head being coupled on opposite end of said tubular element.

3. The measuring device of claim 2 wherein the attachment is tubular and receives in its interior connecting means for connecting the measuring head to the evaluation electronics.

4. The measuring device of claim 3 wherein the attachment has a length and/or a material quality such that the temperature on the measuring head has no effect on the evaluation electronics.

5. The measuring device of claim 1 wherein the measuring head carries a sensor for measuring said electric quality of the material to be measured.

6. The measuring device of claim 5 wherein the measuring head also carries a compensator which compensates the influence of temperature on the sensor and wherein the compensator has the same design as the sensor.

7. The measuring device of claim 5 wherein the sensor is designed for measuring the dielectric constant of the material to be measured.

8. The measuring device of claim 7 wherein the sensor for measuring the dielectric constant comprises two electrodes at least one of which consists of a thin metal wire arranged in an insulated manner on a carrier plate.

9. The measuring device of claim 8 wherein the metal wire is a gold wire.

10. The measuring device of claim 9 wherein the carrier plate consists of ceramic material.

11. The measuring device of claim 5 wherein the attachment, the measuring head, the carrier plate and the sensor consist of a material admissible for being used in conjunction with foods.

12. The measuring device of claim 11 wherein said material is heat resistant up to 230° C.

13. The measuring device of claim 5 wherein the measuring head comprises a cover for the sensor which protects the sensor from making contact with a wall or a bottom of a container for the material to be measured.

14. The measuring device of claim 13 wherein the cover has an edge extending over the sensor.

15. The measuring device of claim 1 wherein the housing has an input unit and a display for displaying parameters entered via the input unit and/or for showing the measured results.

16. The measuring device of claim 15 wherein the display can be switched to selectively show measured results as a numeric value or graphically.

17. The measuring device of claim 16 wherein the evaluation electronics is associated with storage means for storing calibration data or correction data.

18. The measuring device of claim 1 and further including control electronics in said housing, and wherein the evaluation and control electronics comprise a microcontroller.

19. The measuring device of claim 1 and further including control electronics in said housing, and wherein the evaluation and control electronics are associated with an input unit for entering data and/or an output unit for outputting the measured result.

20. The measuring device of claim 19 characterized in that an EEPROM is associated with the evaluation and control electronics for storing data.

* * * * *

UNITED STATES PATENT AND TRADEMARK OFFICE
CERTIFICATE OF CORRECTION

PATENT NO.    : 6,469,521 B1                                Page 1 of 1
DATED         : October 22, 2002
INVENTOR(S)   : Wolfgang Klün et al.

It is certified that error appears in the above-identified patent and that said Letters Patent is hereby corrected as shown below:

Column 7,
Lines 40-44, after "electronics 7" delete "the heat of the material to be measured attachment 11 advantageously has a length between 15 cm and 40 cm, preferably between 25 cm and 35 cm. Tubular attachment 11 advantageously has a diameter between 10 mm and 20 mm."

Column 9,
Line 66, after "on" delete "said" and insert -- an --.

Signed and Sealed this

Twenty-sixth Day of August, 2003

JAMES E. ROGAN
*Director of the United States Patent and Trademark Office*